Sept. 18, 1956 J. M. GARABEDIAN Plant Pat. 1,518

PLUM TREE

Filed Nov. 4, 1955

WITNESS

Addison I. Avery

INVENTOR

John M. Garabedian

Webster & Webster

ATTYS.

United States Patent Office

Plant Pat. 1,518

Patented Sept. 18, 1956

1,518

PLUM TREE

John M. Garabedian, Fresno, Calif.

Application November 4, 1955, Serial No. 545,143

1 Claim. (Cl. 47—62)

This discovery relates to a new and distinct variety of plum tree which bears red clingstone fruit; the variety having general resemblance to the Santa Rosa plum, but being advantageously distinguishable therefrom by certain important characteristics as follows:

The fruit of the present variety of plum tree ripens, on the average, eight to ten days earlier than the Santa Rosa plum; is hardier, holding up well in storage, and of good shipping quality; is larger in size; and is more rounded in form.

The instant variety of plum tree was originated as a seedling of an unnamed yellow fleshed sport of the Santa Rosa plum.

Such sport, the El Dorado plum, and the Mariposa plum were all budded by me onto a single wild plum root stock growing on my property at Fresno, California. When such budded sport came into bearing, as a result of open-pollination and which probably occurred from one of the near-by varieties on the same root stock. I harvested seeds from said sport and planted such seeds in nursery rows on my ranch near Fresno, California.

From the resulting seedlings the present variety was selected by me, for subsequent propagation, as it showed especial promise with respect to fruit characteristics which made it appear very desirable for the commercial market.

Subsequent to selection of the variety, as above, I budded it onto several Lovell peach root stocks growing on my ranch located as aforesaid; such asexual reproductions—when they grew to maturity—having been found to carry forward all of the characteristics of the parent.

Figures 1, 2:
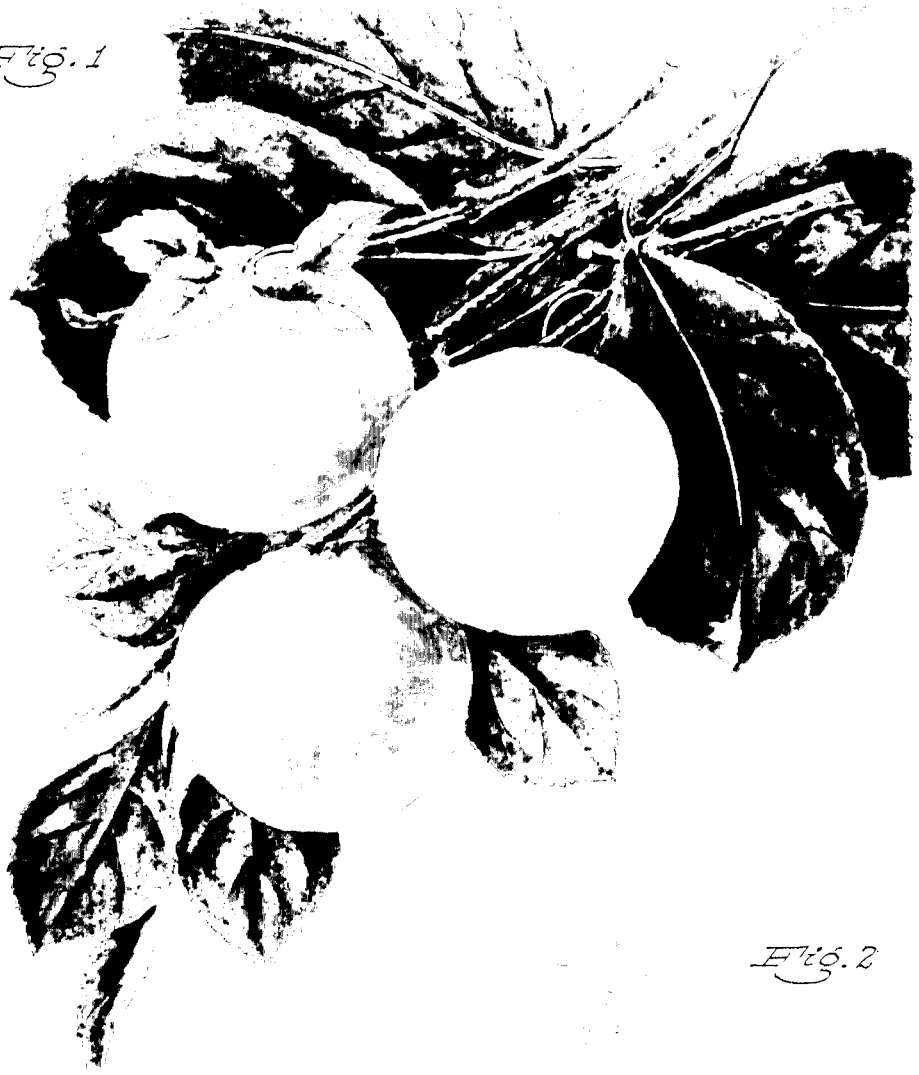
Fig. 1 is an elevation showing a number of the fruit, together with twigs and leaves.
Fig. 2 is a sectional elevation of one of the fruit, with the stone partially exposed.

Referring now more specifically to the pomological details of this new and distinct variety of plum tree, the following is an outline description thereof; all major color plate identifications being by reference to Maerz and Paul Dictionary of Color:

Tree:

*Size.*—Medium.

*Growth.*—Upright to spreading; open; vase formed.

*Production.*—Productive.

*Bearing.*—Uncertain bearer.

Leaves:

*Size.*—Large to medium. Average length—3½" to 6". Average width—1⅝" to 2⅝".

*Form.*—Oval to obovate; acuminate; abruptly pointed.

*Thickness.*—Medium.

*Color.*—Top side—dark green (shading from 23–L–5 to 24–L–7). Under side—lighter green (22–L–7).

*Texture.*—Smooth.

*Margin.*—Doubly-coarse crenate, with one-third to one-half of the crenations tipped with small, reddish-brown to black glands.

*Petiole.*—Medium to short length; medium thickness.

*Glands.*—Average number—two; opposite; medium size; mixed; green. Usually positioned on base of blade; nearly auricular; rarely one gland on the petiole. Stipules—small; linear; margin gland-tipped; light greenish yellow color; form dehiscent.

Flower buds:

*Size.*—Large for the species.

*Length.*—Medium.

*Form.*—Conic to pointed; free.

*Hairs.*—Glabrous.

Flowers:

*Blooming date.*—Medium; i. e., on the early side compared with other varieties.

*Size.*—Medium.

*Color.*—White.

Fruit:

*Maturity when described.*—Eating ripe.

*Date of first picking.*—June 9, 1955.

*Date of last picking.*—June 14, 1955.

*Size.*—Uniform; large to medium. Average diameter axially—1 13/16" to 2 1/16". Average transverse in suture plane—1⅞" to 2 3/16".

*Form.*—Uniform; symmetrical. Round—truncate.

*Suture.*—An inconspicuous to distinct shallow broad groove extending from base to apex.

*Ventral surface.*—Rounded slightly; lips nearly equal.

*Cavity.*—Flaring—rounded. Slightly elongated in suture plane, with suture showing on one side. Average depth—¼" to 5/16". Average breadth—11/16" to ¾". Markings—none.

*Base.*—Rounded—truncate.

*Apex.*—Truncate; depressed at stylar scar.

*Pistil point.*—Apical.

Skin:

*Thickness.*—Medium.

*Texture.*—Tough; tenacious to flesh.

*Flavor.*—Bitter.

*Tendency to crack.*—None observed.

*Down.*—Wanting.

*Color.*—Under color—relatively light red (3–L–2 to 5–L–6), tending to shade to amber. Over color—medium dark red (6–L–6), which over-color becomes considerably darker (45–L–6 to 56–L–12) when standing at room temperature. Relatively numerous small conspicuous dark red dots are evenly scattered laterally, except at the ventral suture and basally where lacking; more numerous and smaller apically. The stylar scar is a brownish dot of medium size. A greyish bloom (42–F–4) is spread over the fruit.

Flesh:

*Amygdalin.*—Wanting.

*Texture.*—Medium; melting.

*Fibers.*—Few; fine; tender.

*Ripens.*—Even.

*Flavor.*—Sub-acid.

*Aroma.*—Distinct.

*Eating quality.*—Best.

*Color.*—Medium red (3–K–10 to 5–L–1), shading to amber (10–I–5), particularly near stone. The colors combine to yield an orange-red effect (2–H–11) in a portion of the flesh, and with increasing ripeness this color deepens towards a darker red (2–K–11).

Stone:

*Type.*—Cling. Adheres to flesh over entire surface.
*Fibers.*—Short.
*Size.*—Medium. Average length—1⅞". Average breadth—11/16" to ¾" in the suture plane. Average thickness—7/16" to ½" cheek to cheek.
*Form.*—Irregularly oval. The stone is very irregular in shape and markings, with the irregularities gross but smoothly rounded; i. e., not rough or jagged.
*Base.*—Straight.
*Hilum.*—Narrow; small.
*Apex.*—Broad, dull point.
*Sides.*—Equal to unequal.
*Surface.*—Irregularly furrowed along ventral edge throughout.
*Ridges.*—Rounded; irregular; continuous.
*Dorsal edge.*—Full with shallow broad groove toward base. Variable, irregular.
*Tendency to split.*—Slight.
*Color.*—Light brown (5–B–11).

Use: Market; dessert.
Keeping quality: Good.
Shipping quality: Good.

The tree and its fruit herein described may vary in slight detail due to climatic and soil conditions under which the variety may be grown.

As far as the applicant is aware none of the prior varieties of plums mentioned herein are patented.

The following is claimed:

A new and distinct variety of plum tree, as illustrated and described, characterized by relatively dark red clingstone fruit whose flesh is medium red shading to amber, and which ripens approximately eight to ten days earlier than the Santa Rosa which it most nearly resembles; the fruit being hardier, larger in size, and more rounded in form than the fruit of said Santa Rosa plum.

No references cited.